United States Patent [19]
Frey et al.

[11] Patent Number: 5,922,864
[45] Date of Patent: Jul. 13, 1999

[54] EFFICIENT SYNTHESIS OF A 1,4-DIHYDRO2H-3,1-BENZOXAZIN-2-ONE

[75] Inventors: Lisa F. Frey, Somerset; Richard D. Tillyer; Edward J. J. Grabowski, both of Westfield, all of N.J.

[73] Assignee: Merck & Co., Inc., Rahway, N.J.

[21] Appl. No.: 09/018,204

[22] Filed: Feb. 3, 1998

Related U.S. Application Data

[60] Provisional application No. 60/037,059, Feb. 12, 1997, abandoned.

[51] Int. Cl.$^6$ .................................................. C07D 265/18
[52] U.S. Cl. ................................. 544/92; 560/27
[58] Field of Search ................................. 544/92; 560/27

[56] References Cited

U.S. PATENT DOCUMENTS 5,519,021  5/1996  Young et al. ........................ 514/230.5

FOREIGN PATENT DOCUMENTS

WO 96/37457  11/1996  WIPO .

OTHER PUBLICATIONS

Uchida, M., et al., Chem. & Pharm. Bull., vol. 38(6), pp. 1575–1586, 1990.

Gouilleux, L., et al., Tetrahedron Letters, vol. 39(37), pp. 7031–7034, 1996.

Pierce et al., Chemical Abstracts, vol. 128, abstract 154087, 1998.

Radesca et al., Chemical Abstracts, vol. 128, abstract 102044, 1998.

*Primary Examiner*—Richard L. Raymond
*Attorney, Agent, or Firm*—Valerie J. Camara; Mark R. Daniel

[57] ABSTRACT

An efficient method for the preparation of a compound of (–)-6-chloro-4-cyclopropylethynyl-4-trifluoromethyl- 1,4-dihydro-2H-3, 1-benzoxazin-2-one, also known as DMP-266, a reverse transcriptase inhibitor is achieved using a cyclization reaction of the amino alcohol intermediate with an alkyl or aryl chloroformate and a base.

27 Claims, No Drawings

EFFICIENT SYNTHESIS OF A 1,4-DIHYDRO2H-3,1-BENZOXAZIN-2-ONE

RELATED APPLICATIONS

This application is based upon U.S. provisional application Ser. No. 60/037,059 filed Feb. 12, 1997 (abandoned).

BACKGROUND OF THE INVENTION

A key step in the synthesis of the reverse transcriptase inhibitor, (−)-6-chloro-4-cyclopropylethynyl-4-trifluoromethyl-1,4-dihydro-2H-3,1-benzoxazin-2-one, also known as DMP-266, is the cyclization of the amino alcohol using phosgene.

The synthesis of DMP-266 and structurally similar reverse transcriptase inhibitors are disclosed in U.S. Pat. No. 5,519,021 and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence that has been described by Thompson, et al., Tetrahedron Letters 1995, 36, 8937–8940, as well as the PCT publication, WO 96/37457, which published on Nov. 28, 1996.

The instant invention discloses an efficient method for the cyclization of an amino alcohol of formula

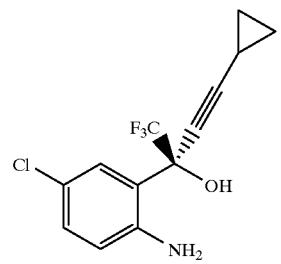

using a chloroformate and a base in a solvent to give the 1,4-dihydro-2H-3,1-benzoxazin-2-one

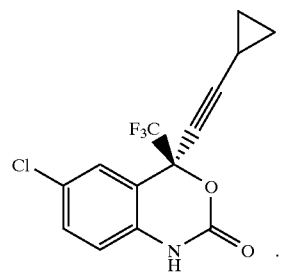

This cyclization method employs an aryl or alkyl chloroformate and avoids the use of phosgene, a toxic and highly hazardous gas, which requires special handling.

SUMMARY OF THE INVENTION

The instant invention relates to an efficient method for the cyclization of an amino alcohol of formula

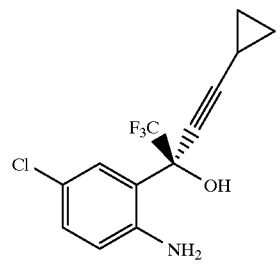

using a chloroformate and a base in a solvent to give the 1,4-dihydro-2H-3,1-benzoxazin-2-one

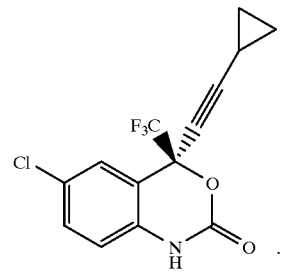

DETAILED DESCRIPTION OF THE INVENTION

The instant invention discloses an efficient process for the preparation of a 1,4-dihydro-2H-3,1-benzoxazin-2-one of the formula

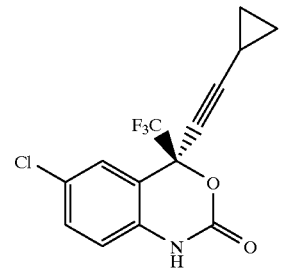

comprising the steps of:

1) adding an aryl chloroformate to a stirring mixture of an amino alcohol of formula

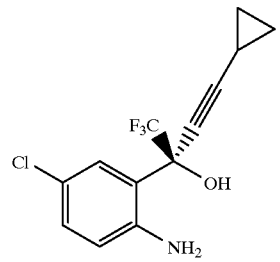

in an organic solvent with a base at a temperature of about 0° C. to about 25° C. under an inert atmosphere to produce a carbamate intermediate of formula

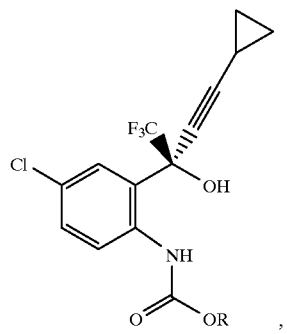

wherein R represents the aryl side chain of the chloroformate;

2) stirring the reaction mixture at about 20° C. to about 25° C. for about 1 to about 6 hours to complete the formation of the carbamate intermediate;

3) quenching the reaction with water or an aqueous base to produce a biphasic solution containing the 1,4-dihydro-2H-3,1-benzoxazin-2-one in the organic solvent phase;

4) stirring the biphasic mixture at about 20° C. to about 50° C. for about 1 to about 6 hours to complete the cyclization to the 1,4-dihydro-2H-3,1-benzoxazin-2-one; and 5) isolating the 1,4-dihydro-2H-3,1-benzoxazin-2-one from the organic phase.

The process for the preparation of a 1,4-dihydro-2H-3,1-benzoxazin-2-one as recited above, wherein the aryl group of the aryl chloroformate is defined as phenyl or naphthyl, which is optionally substituted with one, two or three substituents selected from the group consisting of: halo (F, Cl, Br, I), $CF_3$, $CO_2C_1$–$C_6$-alkyl, and $NO_2$. An embodiment of the aryl chloroformates useful in this process are defined as phenyl chloroformate, in which the phenyl is optionally substituted with one, two or three substituents selected from the group consisting of: halo (F, Cl, Br, I), $CF_3$, and $NO_2$. A preferred aryl chloroformate useful in the process is 4-nitrophenyl chloroformate.

The process for the preparation of a 1,4-dihydro-2H-3,1-benzoxazin-2-one as recited above, wherein the base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases. The process for the preparation of a 1,4-dihydro-2H-3,1-benzoxazin-2-one as recited above, wherein the preferred base is defined as a solid or solution of KOH, NaOH, $K_2CO_3$, $Na_2CO_3$, $KHCO_3$, $NaHCO_3$, or a combination of said bases.

The process for the preparation of a 1,4-dihydro-2H-3,1-benzoxazin-2-one as recited above, wherein the organic solvent is selected form the group consisting of: methyl t-butyl ether, toluene, tetrahydrofuran, acetonitrile dimethylacetamide, N-methylpyrrolidinone, or a combination of said solvents.

A preferred embodiment of the instant invention is the process for the preparation of a 1,4-dihydro-2H-3,1-benzoxazin-2-one of the formula

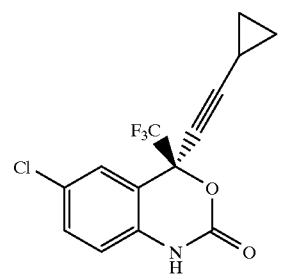

comprising the steps of:

1) adding 4-nitrophenyl chloroformate in batches to a stirring mixture of an amino alcohol of formula

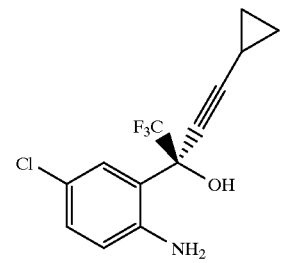

in methyl tert-butyl ether with an aqueous solution of $KHCO_3$ at a temperature of about 25° C. under a nitrogen atmosphere maintaining a pH of between about 8.5 and 4 to produce a carbamate intermediate of formula

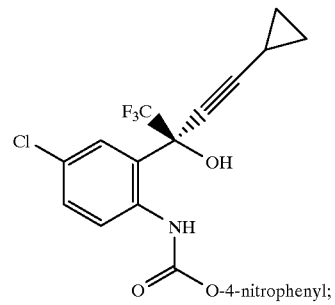

2) stirring the reaction mixture at about 20° C. to about 25° C. for about 2 hours to complete the formation of the carbamate intermediate;

3) quenching the reaction with an aqueous KOH to a pH of about 11 and adding water to produce a biphasic mixture containing the 1,4-dihydro-2H-3,1-benzoxazin-2-one in the organic solvent phase;

4) isolating the 1,4-dihydro-2H-3,1-benzoxazin-2-one from the organic phase.

A process for the preparation of a 1,4-dihydro-2H-3,1-benzoxazin-2-one of the formula

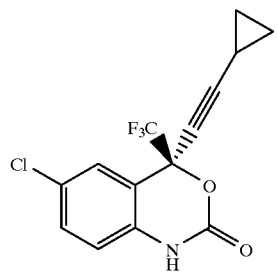

comprising the steps of:
1) adding an aryl chloroformate to a stirring mixture of an amino alcohol of formula

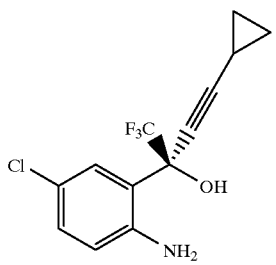

in an organic solvent at a temperature of about 0° C. to about 25° C. under an inert atmosphere to produce a carbamate intermediate of formula

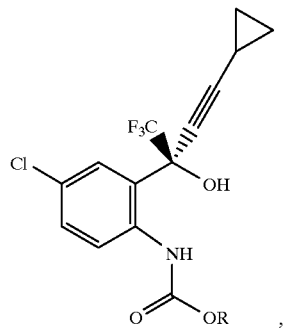

wherein R represents the aryl side chain of the chloroformate;
2) stirring the reaction mixture at about 20° C. to about 25° C. for about 1 to about 6 hours to complete the formation of the carbamate intermediate;
3) quenching the reaction with an aqueous base to produce a biphasic solution containing the 1,4-dihydro-2H-3,1-benzoxazin-2-one in the organic solvent phase;
4) stirring the biphasic mixture at about 20° C. to about 50° C. for about 1 to about 6 hours to complete the cyclization to the 1,4-dihydro-2H-3,1-benzoxazin-2-one; and
5) isolating the 1,4-dihydro-2H-3,1-benzoxazin-2-one from the organic phase.

The process for the preparation of a 1,4-dihydro-2H-3,1-benzoxazin-2-one as recited above, wherein the aryl group of the aryl chloroformate is defined as phenyl or naphthyl, which is optionally substituted with one, two or three substituents selected from the group consisting of: halo (F, Cl, Br, I), $CF_3$, $CO_2C_1$–$C_6$-alkyl, and $NO_2$.

The process for the preparation of a 1,4-dihydro-2H-3,1-benzoxazin-2-one as recited above, wherein the base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases.

The process for the preparation of a 1,4-dihydro-2H-3,1-benzoxazin-2-one as recited above, wherein the organic solvent is selected form the group consisting of: methyl t-butyl ether, toluene, or a combination of said solvents.

The process for the preparation of a 1,4-dihydro-2H-3,1-benzoxazin-2-one as recited above, wherein the aryl group of the aryl chloroformate is defined as phenyl chloroformate, in which the phenyl is optionally substituted with one, two or three substituents selected from the group consisting of: halo (F, Cl, Br, I), $CF_3$, and $NO_2$.

The process for the preparation of a 1,4-dihydro-2H-3,1-benzoxazin-2-one as recited in above, wherein the base is defined as a solid or solution of KOH, NaOH, $K_2CO_3$, $Na_2CO_3$, $KHCO_3$, $NaHCO_3$, or a combination of said bases.

The process for the preparation of a 1,4-dihydro-2H-3,1-benzoxazin-2-one as recited above, wherein the aryl group of the aryl chloroformate is defined as 4-nitrophenyl chloroformate.

Another aspect of the instant invention is the process for the preparation of a 1,4-dihydro-2H-3,1-benzoxazin-2-one of the formula

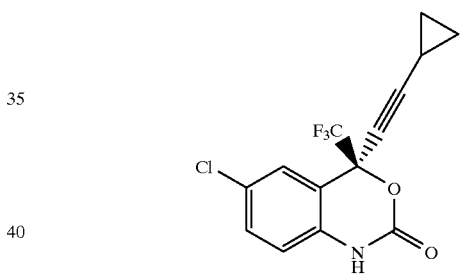

comprising the steps of:

1) adding an alkyl chloroformate to a stirring mixture of an amino alcohol of formula

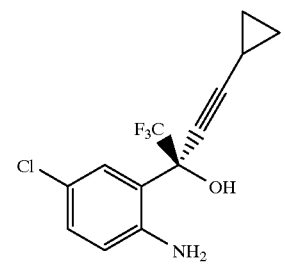

in a first organic solvent with a first base at a temperature of about 0° C. to about 25° C. under an inert atmosphere to produce a carbamate intermediate of formula

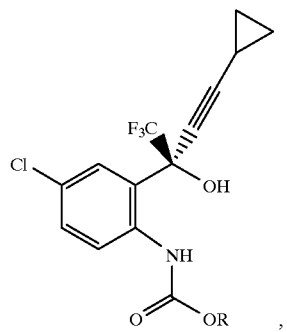

wherein R represents the alkyl side chain of the chloroformate;

2) stirring the reaction mixture at about 20° C. to about 25° C. for about 1 to about 30 hours to complete the formation of the carbamate intermediate;

3) isolating the organic phase containing the alkyl carbamate;

4) distilling about 90% to about 95% of the first organic solvent in vacuum and adding a counter solvent to isolate the solid alkyl carbamate;

5) adding a second organic solvent to the solid alkyl carbamate to form an alkyl carbamate solution;

6) reacting the alkyl carbamate solution with a second base at a temperature range of about 20° C. to about 25° C. for about 2 hours to about 30 hours to produce the 1,4-dihydro-2H-3,1-benzoxazin-2-one;

7) quenching the reaction mixture with an acid to produce a biphasic solution containing the 1,4-dihydro-2H-3,1-benzoxazin-2-one in the organic solvent phase;

8) isolating the 1,4-dihydro-2H-3,1-benzoxazin-2-one from the organic phase.

The process for the preparation of a 1,4-dihydro-2H-3,1-benzoxazin-2-one as recited above, wherein the alkyl group of the alkyl chloroformate is defined as $C_1$–$C_{10}$-alkyl, which is optionally substituted with one, two or three substituents selected from the group consisting of: halo (F, Cl, Br, I), $CF_3$, $C_3$–$C_7$-cycloalkyl, $CO_2C_1$–$C_6$-alkyl, and $NO_2$. An embodiment of the alkyl choroformates useful in the process for the preparation of a 1,4-dihydro-2H-3,1-benzoxazin-2-one as recited above, are methyl or ethyl chloroformate.

The process for the preparation of a 1,4-dihydro-2H-3,1-benzoxazin-2-one as recited above, wherein the first base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases. The process for the preparation of a 1,4-dihydro-2H-3,1-benzoxazin-2-one as recited above, wherein the second base is defined as a solid or solution of $KOC_1$–$C_6$-alkyl, $NaOC_1$–$C_6$-alkyl, $LiOC_1$–$C_6$-alkyl, $KC_1$–$C_6$-alkyl, $NaC_1$–$C_6$-alkyl, $LiC_1$–$C_6$-alkyl, KHMDS, NaHMDS, LiHMDS, LDA or a combination of said bases.

The process for the preparation of a 1,4-dihydro-2H-3,1-benzoxazin-2-one as recited above, wherein the first organic solvent is selected form the group consisting of: methyl t-butyl ether, toluene, tetrahydrofuran, acetonitrile, or a combination of said solvents. The process for the preparation of a 1,4-dihydro-2H-3,1-benzoxazin-2-one as recited above, wherein the counter solvent is heptane. The process for the preparation of a 1,4-dihydro-2H-3,1-benzoxazin-2-one as recited above, wherein the second organic solvent is selected form the group consisting of: methyl t-butyl ether, toluene, tetrahydrofuran, $C_1$–$C_6$-alkanol, or a combination of said solvents.

The process for the preparation of a 1,4-dihydro-2H-3,1-benzoxazin-2-one as recited above, wherein the acid is selected form the group consisting of: HCl, $HNO_3$, $H_2SO_4$, and $CH_3CO_2H$.

The process for the preparation of 1,4-dihydro-2H-3,1-benzoxazin-2-one as recited above, comprising the additional step of: crystallizing the alkyl carbamate produced in step 4 from toluene-heptane or methyl t-butyl ether-heptane to produce the crystalline alkyl carbamate.

Another aspect of the invention is an alkyl carbamate of formula

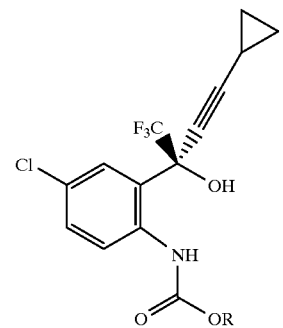

wherein R represents $C_1$–$C_{10}$-alkyl, which is optionally substituted with one, two or three substituents selected from the group consisting of: halo (F, Cl, Br, I), $CF_3$, $C_3$–$C_7$-cycloalkyl, $CO_2C_1$–$C_6$-alkyl, and $NO_2$.

As used herein, the term "alkyl" includes those alkyl groups of a designated number of carbon atoms of either a straight, branched, or cyclic configuration and optionally substituted with a substituent selected from the group consisting of: halo (F, Cl, Br, I), $CF_3$, $CO_2C_1$–$C_6$-alkyl, $C_3$–$C_7$-cycloalkyl, and $NO_2$. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. The term "aryl" is defined as a phenyl or naphthyl ring which is optionally substituted one, two or three substitutents at any available carbon atoms selected from the group consisting of: halo (F, Cl, Br, I), $CF_3$, $CO_2C_1$–$C_6$-alkyl, and $NO_2$.

The term inert atmosphere is understood to be an atmosphere of argon or nitrogen, preferrably nitrogen.

Scheme 1 outlines the key steps in the synthesis of (−)-6-chloro-4-cyclopropylethynyl-4-trifluoromethyl- 1,4-dihydro-2H-3,1-benzoxazin-2-one (DMP-266). The chiral addition step allows for the enantioselective addition of the cyclopropylacetylide across the trifluoromethylketone of 1. The PMB-protected amino alcohol, 2, produced is then deprotected to give the amino alcohol, 3. The amino alcohol is then cyclized using a chloroformate and base to give DMP-266.

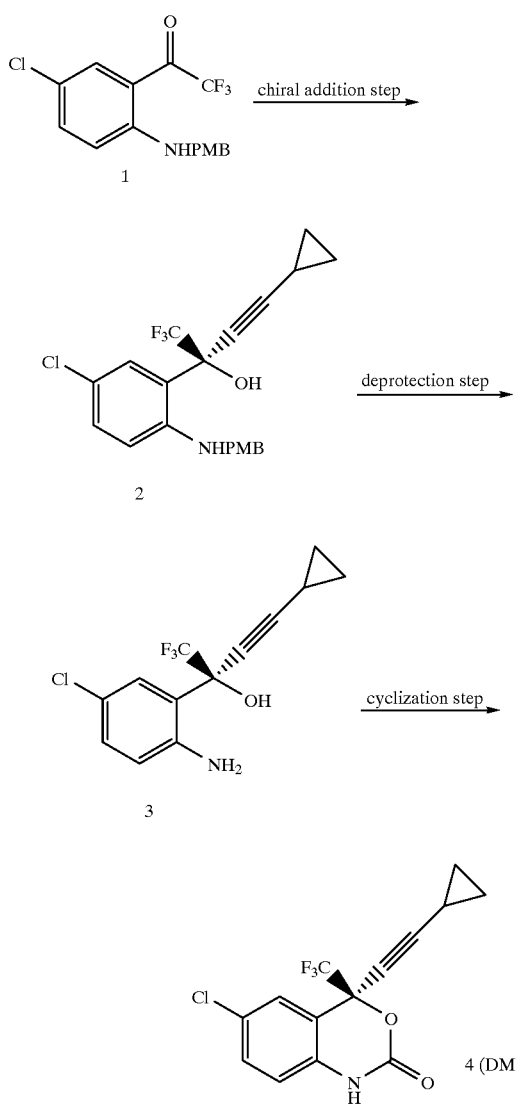

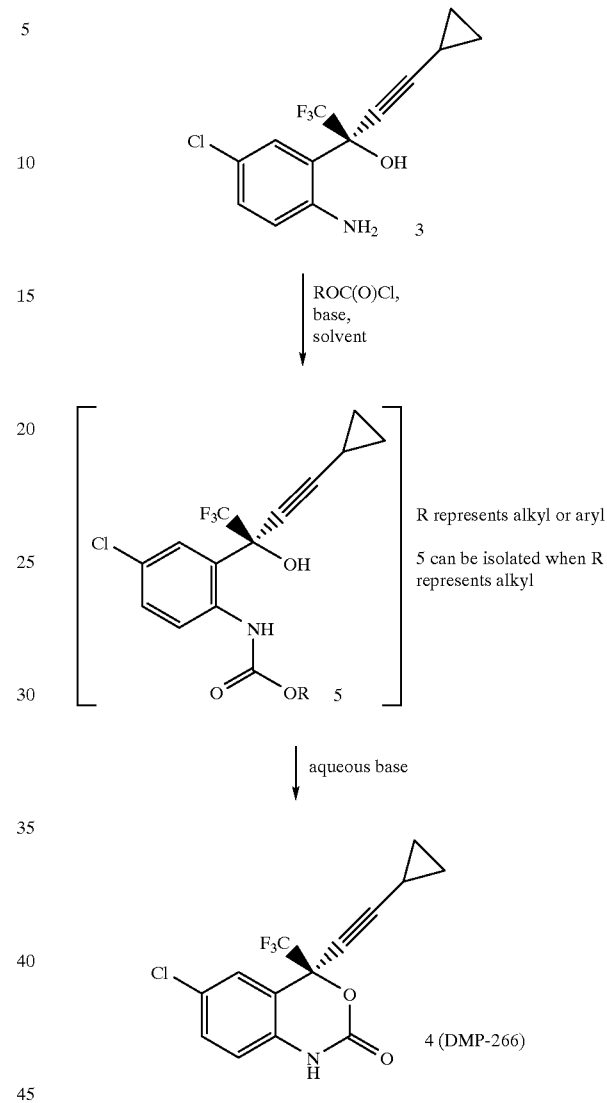

The cyclization of the amino alcohol, 3 to produce the 1,4-dihydro-2H-3,1-benzoxazin-2-one, 4 is outlined in Scheme 2 below. The reaction can be carried out as a one-step process, or alternatively a two step process with the potential isolation of the intermediate carbamate, 5 depending upon the chloroformate utilized. It has been demonstrated that the aryl chloroformates form less stable carbamates such that when they are treated with aqueous base they cyclize to the product, in a one-step process. The alkyl chloroformate, alternatively, provides an alkyl carbamate, a key intermediate capable of being isolated and purified prior to carrying out the cyclization step. Based upon the stability of the alkyl carbamates, a viable two step process for the preparation of DMP-266 has been developed which comprises the formation of the alkyl carbamate intermediate, 5 followed by the cyclization of the carbamate to give the desired product, 4.

Table 1 lists the solvents and bases which can be used when running a one step process employing an aryl chloroformate. Additionally, combination of the bases listed below can and have been used, such as, bicarbonate and hydroxide, or bicarbonate and carbonate. The reaction can be run as a monophasic or biphasic reaction mixture. The base can be added at the start of the addition of the chloroformate or alternatively, after the aryl chloroformate addition is complete. The base is preferably added at the start of the addition of the aryl chloroformate to quench the hydrogen chloride as it is produced.

TABLE 1

| One Step Process | |
|---|---|
| solvent | base |
| ACN | carbonates(s) |
| | bicarbonates(s) |
| | hydroxides(s) |

TABLE 1-continued

One Step Process

| solvent | base |
|---|---|
| DMAC | carbonates(s) |
| | bicarbonates(s) |
| | hydroxides(s) |
| MTBE | carbonates(aq) |
| | bicarbonates(aq) |
| | hydroxides(aq) |
| NMP | carbonates(s) |
| | bicarbonates(s) |
| | hydroxides(s) |
| THF | carbonates(s) |
| | bicarbonates(s) |
| | hydroxides(s) |
| TOL | carbonates(aq) |
| | bicarbonates(aq) |
| | hydroxides(aq) |

Table 2 lists the solvents and bases which can be used when running two-step process employing an alkyl chloroformate. Step one of the two-step process, the formation of the alkylcarbamate, can be carried out as a monophasic or biphasic reaction mixture. Step two of the two-step process, ring closure of the alkyl carbamate, can be carried out in the solvents noted using the listed bases.

TABLE 2

Two Step Process

| Step 1: Carbamate Formation | | Step 2: Ring Closure | |
|---|---|---|---|
| 1st solvent | 1st base | 2nd solvent | 2nd base |
| ACN† | carbonates(s) | alcohol | alkoxide |
| | bicarbonates(s) | THF | alkoxide |
| | hydroxides(s) | | alkyl alkaline metal |
| THF | carbonates(s) | | alkaline metal HMDS |
| | bicarbonates(s) | | LDA |
| | hydroxides(s) | MTBE | alkoxide |
| MTBE* | carbonates(aq) | | alkyl alkaline metal |
| | bicarbonates(aq) | | alkaline metal HMDS |
| | hydroxides(aq) | | LDA |
| TOL* | carbonates(aq) | TOL | alkoxide |
| | bicarbonates(aq) | | alkyl alkaline metal |
| | hydroxides(aq) | | alkaline metal HMDS |
| | | | LDA |

†Use of acetonitrile as the first base may require an alternate isolation procedure, such as distilling the acetonitrile and cooling to effect crystallization of the carbamate, as opposed to distilling most of the first organic solvent, and then adding a counter solvent to crystallize the carbamate.
*biphasic reaction mixtures.
s refers to solid, when solid base is utilized in an anhydrous reaction mixture then the reaction is followed by a water quench.
aq refers to an aqueous solution of the base.

Abbreviations for the solvents: acetonitrile (ACN); $C_1$–$C_6$-alcohol (alcohol); dimethylacetamide (DMAC); methyl t-butyl ether (MTBE); N-methylpyrrolidinone (NMP); tetrahydrofuran (THF); and toluene (TOL). Additionally, mixtures of the recited solvents may be used to optimize the reaction.

Abbreviations for the bases: lithium, sodium and potassium hydroxides; lithium, sodium and potassium carbonates; lithium, sodium and potassium bicarbonates; lithium, sodium and potassium alkyl (e.g. n-butyl lithium); lithium, sodium and potassium hexamethyldisilazide (e.g. LiHMDS); and lithium diisopropylamide (LDA).

The following examples are meant to be illustrative of the present invention. These examples are presented to exemplify the invention and are not to be construed as limiting the scope of the invention.

EXAMPLE 1

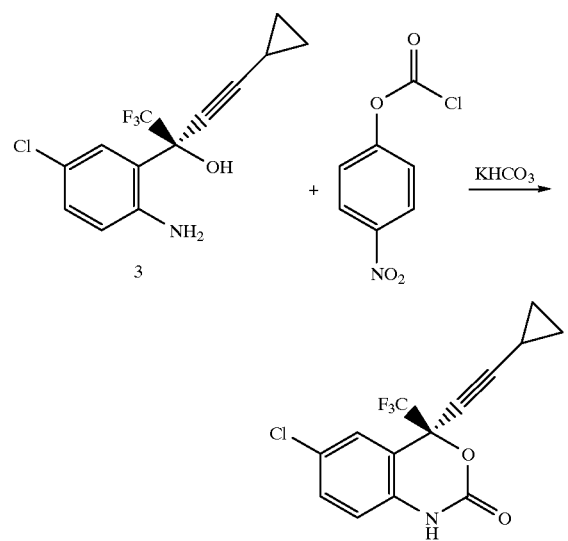

| | FW | g | mL | mmol | equiv |
|---|---|---|---|---|---|
| amino alcohol 12 | 289 | 7.0 | | 24.2 | 1 |
| 4-nitrophenyl chloroformate | 201.6 | 5.9 | | 29.3 | 1.2 |
| $KHCO_3$ | 100 | 7.26 | | 72.6 | 3 |
| $K_2CO_3$ | 138 | 10 | | 72.5 | 3 |
| H2O | | | 250 | | |
| THF | | | 100 | | |
| MTBE | | | 100 | | |
| EtOH | | | 45 | | |

To a three necked round bottom flask, equipped with a mechanical stirrer, nitrogen line, and thermocouple, was charged the solid amino alcohol 3, THF (100 mL), and solid $KHCO_3$. The resulting mixture was cooled to +5° C. and then solid 4-nitrophenyl chloroformate was added, in a single batch. This reaction is exothermic. A temperature rise of 4 degrees (final temp 9° C.) was observed as the nitrophenyl chloroformate dissolved/reacted. The mixture was stirred at 20–25° C. for two hours. A sample was taken from the batch and diluted with ACN and 5% $NaHCO_3$, to make a yellow, homogeneous solution. HPLC analysis at 220 nm showed nitrophenol (43%), 4 (49%), nitrophenyl carbonate (7%) and several low level (<0.3%) impurities. Sampling the batch and diluting in this manner is important for reproducible data. If a sample of the batch is diluted with ACN and analyzed by HPLC, the major peak is that due to the nitrophenyl carbamate 5. This is converted to 4 upon addition of aqueous base.

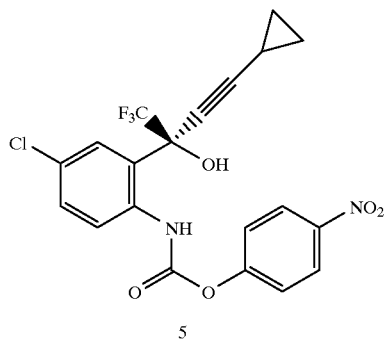

5

The reaction was quenched by addition of aq $K_2CO_3$ (10 g in 150 mL $H_2O$). The resulting two phase mixture was stirred vigorously at 25° C. for two hours. MTBE (100 mL) was then added, the layers were separated, and the organic layer was washed with 5% aqueous $K_2CO_3$ (2×50 mL) and $H_2O$ (2×50 mL). The solvent was switched to ethanol (EtOH) or isopropanol (IPA), and the product crystallized from EtOH or IPA and water. See Examples 10 and 11.

EXAMPLE 2

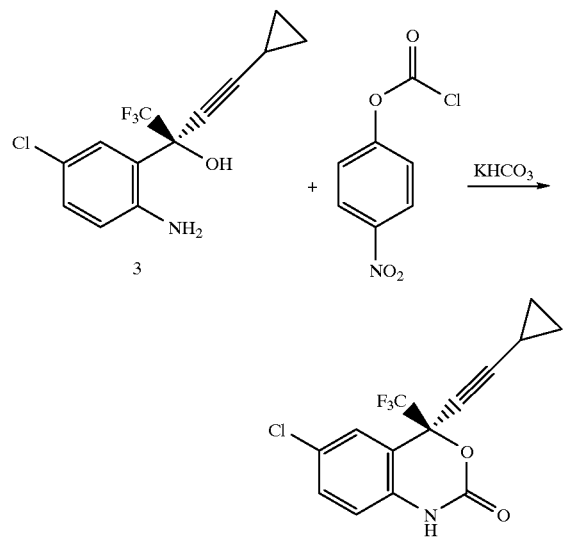

| | FW | g | mL | mmol | eq. |
|---|---|---|---|---|---|
| amino alcohol 12 | 289 | 7.0 | | 24.2 | 1 |
| 4-nitrophenylchloroformate | 201.6 | 5.9 | | 29.3 | 1.2 |
| $K_2CO_3$ | 138 | 20 | | 145.2 | 6 |
| H2O | | | 370 | | |
| MTBE | | | 100 | | |
| EtOH | | | 45 | | |

To a three necked round bottom flask, equipped with a mechanical stirrer, N2 line, and thermocouple was charged the solid amino alcohol 12, MTBE (100 mL), and aq $K_2CO_3$ (10 g in 120 mL $H_2O$, 3 equiv.). Solid 4-nitrophenyl chloroformate was added, in a single batch, at 25° C. The mixture was stirred at 20–25° C. for two hours. At this point the two phase mixture was heated to 50° C. for 3 h, in order to effect conversion of nitrophenyl carbonate to nitrophenol. After cooling to 25° C., the layers were separated and the MTBE layer was extracted with aq $K_2CO_3$ (10 g in 150 mL $H_2O$, in two 75 mL portions) and then with water (2×50 ml). At this point the mixture was solvent switched to EtOH/IPA and crystallized as noted in Examples 10 and 11.

EXAMPLE 3

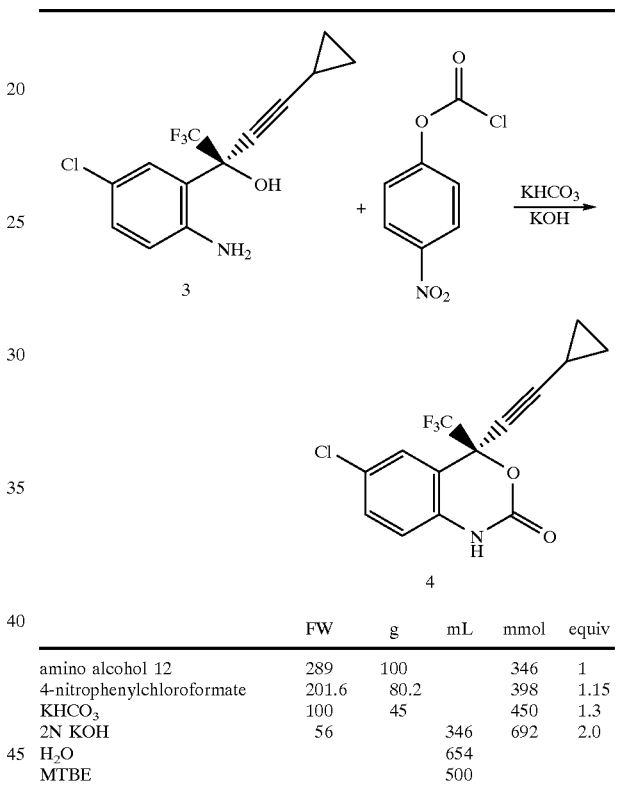

| | FW | g | mL | mmol | equiv |
|---|---|---|---|---|---|
| amino alcohol 12 | 289 | 100 | | 346 | 1 |
| 4-nitrophenylchloroformate | 201.6 | 80.2 | | 398 | 1.15 |
| $KHCO_3$ | 100 | 45 | | 450 | 1.3 |
| 2N KOH | 56 | | 346 | 692 | 2.0 |
| $H_2O$ | | | 654 | | |
| MTBE | | | 500 | | |

To a three necked round bottom flask, equipped with a mechanical stirrer, nitrogen line, and thermocouple, was charged the solid amino alcohol 3, MTBE (500 mL), and aqueous $KHCO_3$ (45 g in 654 mL $H_2O$). Solid 4-nitrophenyl chloroformate was added, in 4 batches, at 25° C. During the addition the solution pH was monitored. The pH was maintained between 8.5 and 4 during the reaction and ended up at 8.0. The mixture was stirred at 20–25° C. for two hours. Aqueous KOH (2N) was added over 20 minutes, until the pH of the aqueous layer reached 11.0.

The layers were separated and the MTBE layer was washed with pH7 buffer (500 mL) and brine (500 mL). At this point the mixture was solvent switched to EtOH/IPA and crystallized as recited in Examples 10 and 11.

EXAMPLE 4

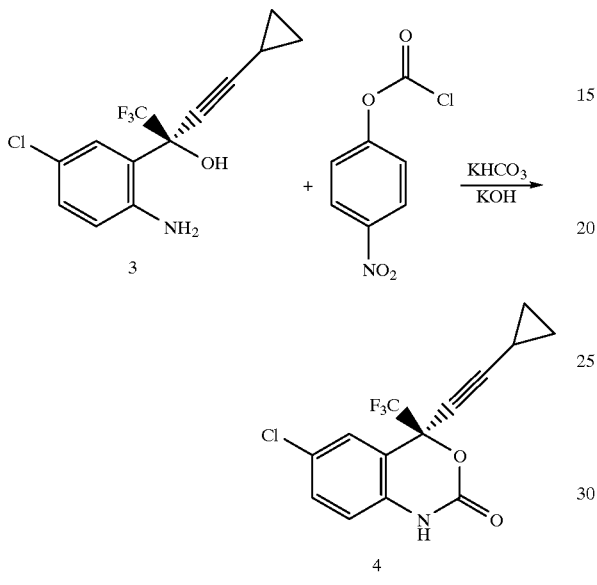

| | FW | g | mL | mmol | equiv |
|---|---|---|---|---|---|
| amino alcohol 3 | 289 | 100 | | 346 | 1 |
| 4-nitrophenylchloroformate | 201.6 | 73.2 | | 363 | 1.05 |
| KHCO$_3$ | 100 | 45 | | 450 | 1.3 |
| 2N KOH | 56 | | 346 | 692 | 2.0 |
| H$_2$O | | | 654 | | |
| MTBE | | | 500 | | |

To a three necked round bottom flask, equipped with a mechanical stirrer, nitrogen line, and thermocouple, was charged the solid amino alcohol 3, MTBE (500 mL), and aqueous KHCO$_3$ (45 g in 654 mL H$_2$O). Solid 4-nitrophenyl chloroformate was added, in 4 batches, at 25° C. During the addition the solution pH was monitored. The pH was maintained between 8.5 and 4 during the reaction and ended up at 8.0. The mixture was stirred at 20–25° C. for two hours. Aqueous KOH (2N) was added over 20 minutes, until the pH of the aqueous layer reached 11.0.

The layers were separated and 500 mL brine was added to the MTBE layer. 0.1N Acetic acid was added until the pH was 6–7. The layers were separated and the organic phase was washed with brine (500 mL). At this point the mixture was solvent switched to EtOH/IPA and crystallized as recited in Examples 10 and 11.

EXAMPLE 5

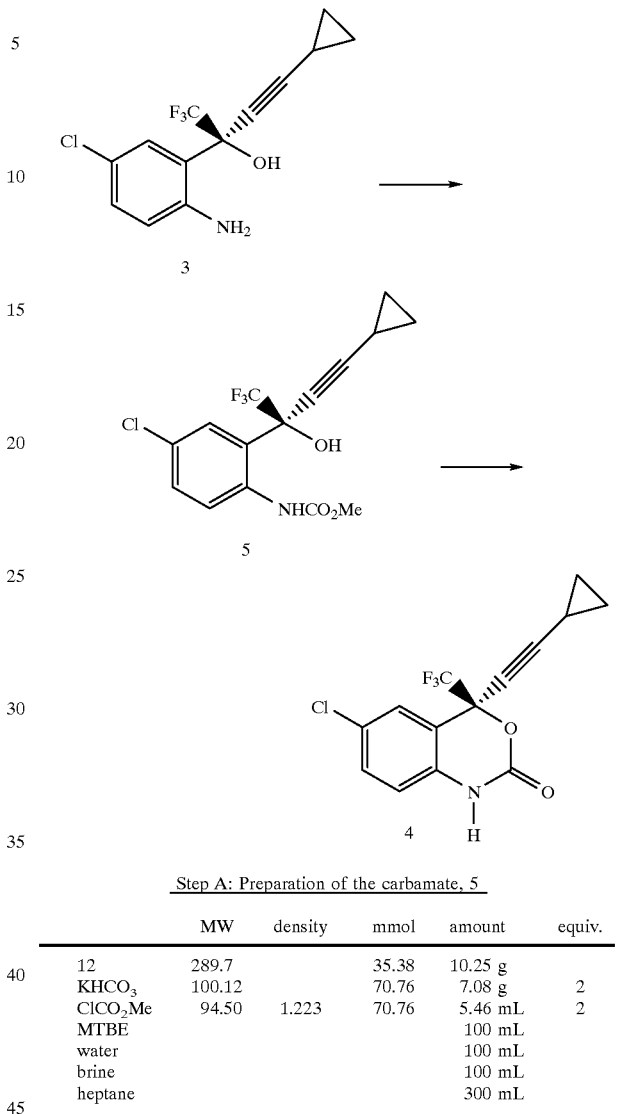

Step A: Preparation of the carbamate, 5

| | MW | density | mmol | amount | equiv. |
|---|---|---|---|---|---|
| 12 | 289.7 | | 35.38 | 10.25 g | |
| KHCO$_3$ | 100.12 | | 70.76 | 7.08 g | 2 |
| ClCO$_2$Me | 94.50 | 1.223 | 70.76 | 5.46 mL | 2 |
| MTBE | | | | 100 mL | |
| water | | | | 100 mL | |
| brine | | | | 100 mL | |
| heptane | | | | 300 mL | |

A 500 mL 3-neck round bottom flask was equipped with an overhead stirrer, temperature probe, and nitrogen line. The amino alcohol 3 (35.38 mmol, 10.25 g) and MTBE (100 mL) were charged, forming a light slurry. The water (100 mL) was charged, followed by potassium bicarbonate (2 equ, 7.08 g). Methyl chloroformate (2 equiv., 5.46 mL) was charged via syringe, and the biphasic mixture was stirred vigorously at 20–25° C. Samples were assayed by HPLC until <0.5% amino alcohol 3 remained (approximately 8.5 hours). The layers were separated, and the organic layer was washed with brine (100 mL) and dried over magnesium sulfate. After filtration, a solvent switch (50–60° C. under vacuum) was carried out into a MTBE—heptane mixture (approx. 5% MTBE by volume as measured by $^1$H NMR) of 102 mL (10 mL/g starting material) total volume. The methyl carbamate 5 crystallized readily during the solvent switch. After aging the slurry at 20–25° C. for approx. 30 min, the material was filtered. The solid was washed with the mother liquors, and then with one cake volume of heptane. The dry methyl carbamate 5 was isolated in 92% yield (11.32 g). 1–2% was lost to the mother liquors.

Step B: Preparation of the ring closed compound, 4

|  | MW | density | mmol | amount | equiv. |
|---|---|---|---|---|---|
| 5 | 347.72 |  | 32.55 | 11.32 g |  |
| 1M LiO$^t$Bu |  |  | 32.55 | 32.6 mL | 1 |
| MTBE |  |  |  | 170 mL |  |
| 0.5 N HCl |  |  |  | 150 mL |  |
| brine |  |  |  | 150 mL |  |

A 500 mL 3-neck round bottom flask was equipped with an overhead stirrer, temperature probe, and nitrogen line. The methyl carbamate 5 (32.55 mmol, 11.32 g) was dissolved in MTBE (170 mL). LiO$^t$Bu (1 equiv., 32.6 mL) was charged, and the reaction mixture immediately became a slurry. The slurry thinned with time and was a clear yellow solution within 30 min. The reaction mixture was aged at 20–25° C. The reaction was followed by HPLC. After 8 h, <1% methyl carbamate 5 remained. In approximately 16 hours, less than 0.3% methyl carbamate 5 remained. The reaction was quenched into 0.5N HCl (150 mL). The layers were separated, and the organic layer was washed with brine (150 mL), dried over magnesium sulfate, and filtered. The HPLC assay yield was 96.0% of 4. The material was solvent switched into EtOH in preparation for an EtOH-water crystallization. See Examples 10 and 11.

EXAMPLE 6

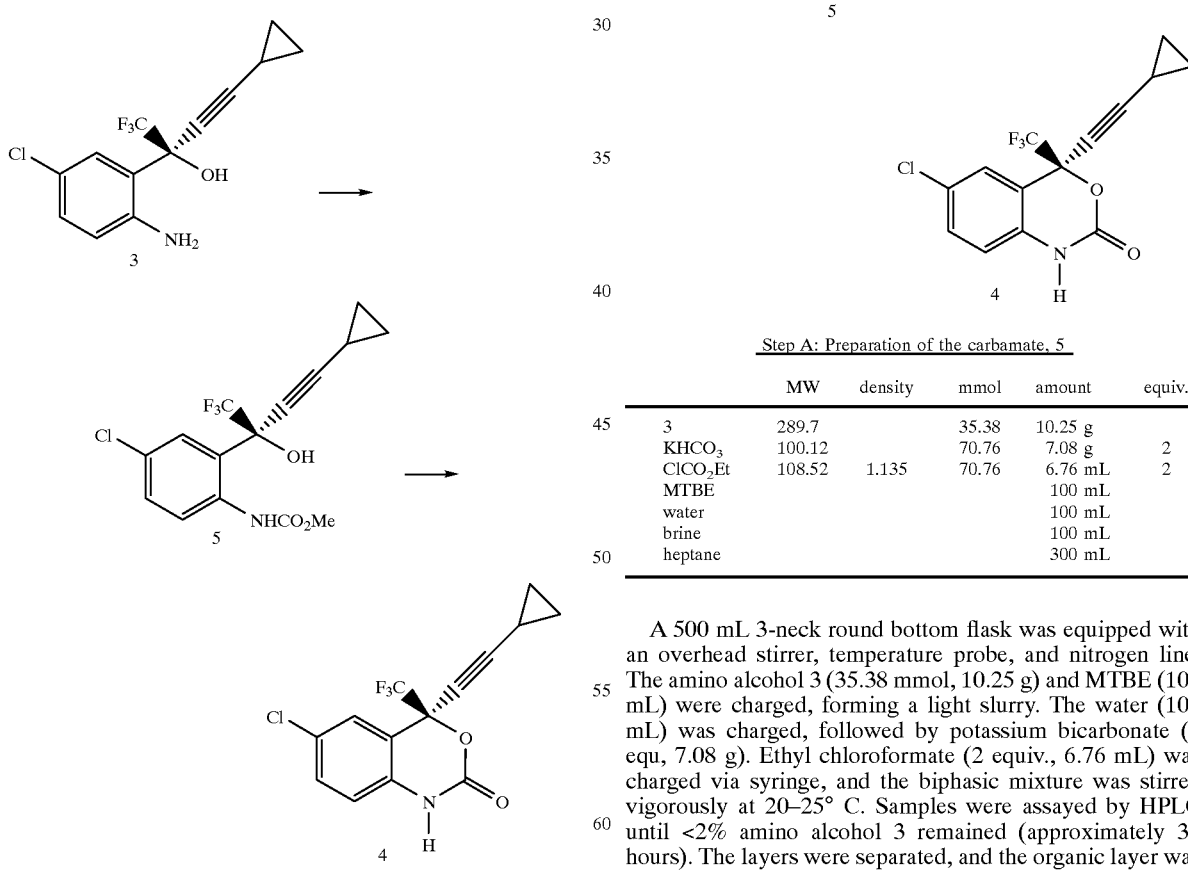

Step A: Preparation of the carbamate, 5

Following the procedure as recited in Example 5, Step A except using toluene as the solvent, and isolation the carbamate from a mixture of toluene-heptane.

Step B: Preparation of the ring closed compound, 4

Following the procedure as recited in Example 5, Step B except using toluene as the solvent, and isolating the product, 4 by crystallization from a mixture of toluene-heptane.

EXAMPLE 7

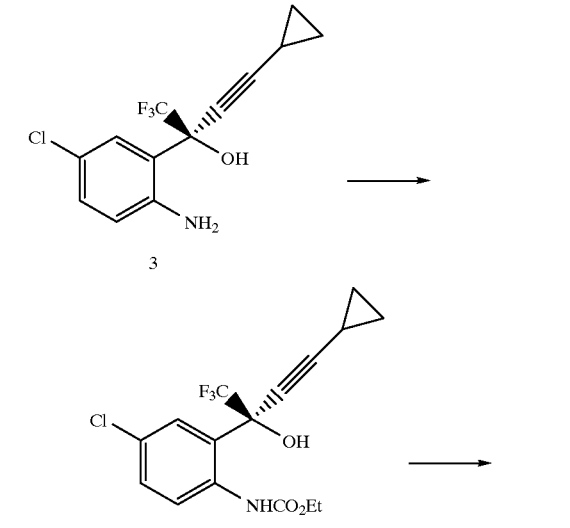

Step A: Preparation of the carbamate, 5

|  | MW | density | mmol | amount | equiv. |
|---|---|---|---|---|---|
| 3 | 289.7 |  | 35.38 | 10.25 g |  |
| KHCO$_3$ | 100.12 |  | 70.76 | 7.08 g | 2 |
| ClCO$_2$Et | 108.52 | 1.135 | 70.76 | 6.76 mL | 2 |
| MTBE |  |  |  | 100 mL |  |
| water |  |  |  | 100 mL |  |
| brine |  |  |  | 100 mL |  |
| heptane |  |  |  | 300 mL |  |

A 500 mL 3-neck round bottom flask was equipped with an overhead stirrer, temperature probe, and nitrogen line. The amino alcohol 3 (35.38 mmol, 10.25 g) and MTBE (100 mL) were charged, forming a light slurry. The water (100 mL) was charged, followed by potassium bicarbonate (2 equ, 7.08 g). Ethyl chloroformate (2 equiv., 6.76 mL) was charged via syringe, and the biphasic mixture was stirred vigorously at 20–25° C. Samples were assayed by HPLC until <2% amino alcohol 3 remained (approximately 30 hours). The layers were separated, and the organic layer was washed with brine (100 mL) and dried over magnesium sulfate. After filtration, a solvent switch (50–60° C. under vacuum) was carried out into a MTBE—heptane mixture (approx. 5% MTBE by volume as measured by $^1$H NMR) of 102 mL (10 mL/g starting material) total volume. The ethyl carbamate 5 crystallized readily during the solvent switch.

After aging the slurry at 20–25° C. for approx. 30 min, the material was filtered. The solid was washed with the mother liquors, and then with one cake volume of heptane. The dry ethyl carbamate 5 was isolated in 92% yield (11.77 g). 1–2% was lost to the mother liquors.

Step B: Preparation of the ring closed compound, 4

|   | MW | density | mmol | amount | equiv. |
|---|---|---|---|---|---|
| 5 | 361.75 |  | 32.55 | 11.77 g |  |
| 1M LiO$^t$Bu |  |  | 32.55 | 32.6 mL | 1 |
| MTBE |  |  |  | 170 mL |  |
| 0.5 N HCl |  |  |  | 150 mL |  |
| brine |  |  |  | 150 mL |  |

A 500 mL 3-neck round bottom flask was equipped with an overhead stirrer, temperature probe, and nitrogen line. The ethyl carbamate 5 (32.55 mmol, 11.32 g) was dissolved in MTBE (170 mL). LiO$^t$Bu (1 equiv., 32.6 mL) was charged, and the reaction mixture immediately became a slurry. The slurry thinned with time and was a clear yellow solution within 30 min. The reaction mixture was aged at 20–25° C. The reaction was followed by HPLC. After 26 h, <1% ethyl carbamate 5 remained. The reaction was quenched into 0.5N HCl (150 mL). The layers were separated, and the organic layer was washed with brine (150 mL), dried over magnesium sulfate, and filtered. The HPLC assay yield was 96.0% of 4. The material was solvent switched into EtOH in preparation for an EtOH-water crystallization. See Examples 10 and 11.

EXAMPLE 8

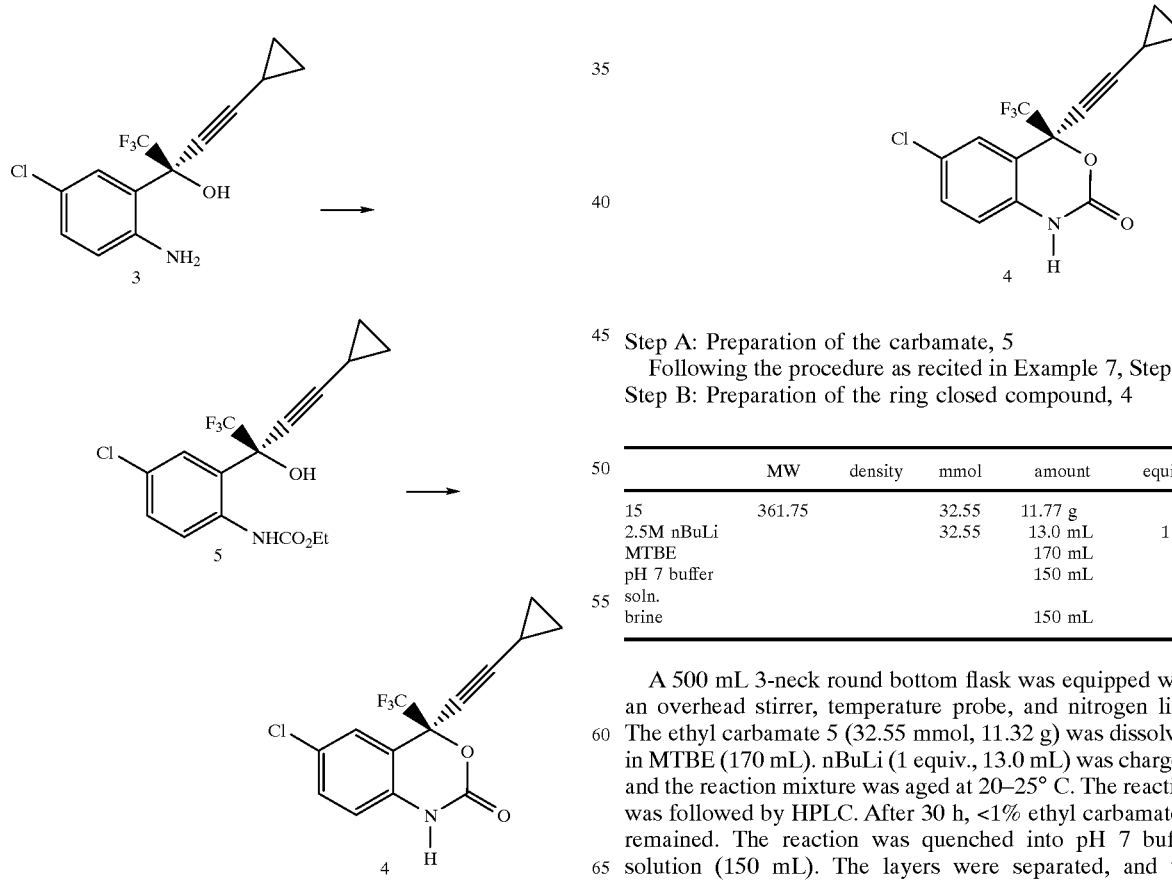

Step A: Preparation of the carbamate, 5

Following the procedure as recited in Example 7, Step A except using toluene as the solvent, and isolation the carbamate from a mixture of toluene-heptane.

Step B: Preparation of the ring closed compound, 4

Following the procedure as recited in Example 7, Step B except using toluene as the solvent, and isolating the product, 4 by crystallization from toluene-heptane.

EXAMPLE 9

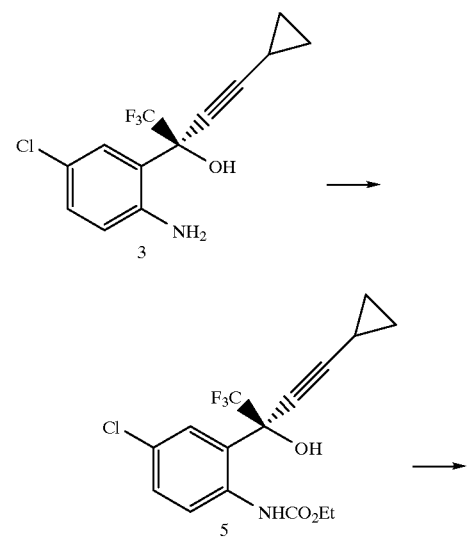

Step A: Preparation of the carbamate, 5

Following the procedure as recited in Example 7, Step A.

Step B: Preparation of the ring closed compound, 4

|   | MW | density | mmol | amount | equiv. |
|---|---|---|---|---|---|
| 15 | 361.75 |  | 32.55 | 11.77 g |  |
| 2.5M nBuLi |  |  | 32.55 | 13.0 mL | 1 |
| MTBE |  |  |  | 170 mL |  |
| pH 7 buffer soln. |  |  |  | 150 mL |  |
| brine |  |  |  | 150 mL |  |

A 500 mL 3-neck round bottom flask was equipped with an overhead stirrer, temperature probe, and nitrogen line. The ethyl carbamate 5 (32.55 mmol, 11.32 g) was dissolved in MTBE (170 mL). nBuLi (1 equiv., 13.0 mL) was charged, and the reaction mixture was aged at 20–25° C. The reaction was followed by HPLC. After 30 h, <1% ethyl carbamate 5 remained. The reaction was quenched into pH 7 buffer solution (150 mL). The layers were separated, and the organic layer was washed with brine (150 mL), dried over magnesium sulfate, and filtered. The HPLC assay yield was 96.0% of 4. The material was solvent switched into EtOH in preparation for an EtOH-water crystallization. See Examples 10 and 11.

EXAMPLE 10

Controlled Anti-Solvent Addition Crystallization Process 400 g. of DMP-266 starting material is dissolved in 2.400 L of ethanol. The solution is filtered to remove extraneous matter. 2.088 L of deionized (DI) water is added to the solution over 30 to 60 minutes. 20 g. of DMP-266 seed is added to the solution. The seed bed is aged for 1 hour. The use of Intermig agitators is preferred to mix the slurry. If required (by the presence of extremely long crystals or a thick slurry), the slurry is wet-milled for 15–60 seconds. 1.512 L of DI water is added to the slurry over 4 to 6 hours. If required (by the presence of extremely long crystals or a thick slurry), the slurry is wet-milled for 15 to about 60 seconds during the addition. The slurry is aged for 1 to 3 hours before being cooled to 10° C. over 3 hours. The slurry is aged for 2 to 16 hours until the product concentration in the supernatant remains constant. The slurry is filtered to isolate a crystalline wet cake. The wet cake is washed with 1 to 2 bed volumes of 40% ethanol in water and then twice with 2 L of DI water each. The washed wet cake is dried under vacuum at 50° C.

EXAMPLE 11

Semi-Continuous Heel Crystallization Process 400 g. of DMP-266 starting material is dissolved in 2.400 L of ethanol. A heel slurry is produced by mixing 20 g of DMP-266 in 0.3 L of 40% (v/v) ethanol in water. The dissolved batch and 3.6 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is cooled to about 10° C. over 3 hours. The slurry is aged for 2 to 16 hours until the product concentration in the supernatant remains constant. The slurry is filtered to isolate a crystalline wet cake. The wet cake is washed with 1 to 2 bed volumes of 40% ethanol in water and then twice with 2 L of DI water each. The washed wet cake is dried under vacuum at 50° C.

What is claimed is:

1. A process for the preparation of a 1,4-dihydro-2H-3,1-benzoxazin-2-one of the formula

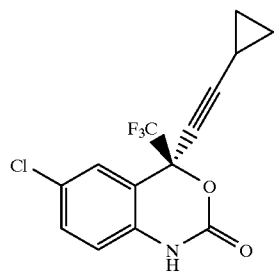

comprising the steps of:

1) adding an aryl chloroformate to a stirring mixture of an amino alcohol of formula

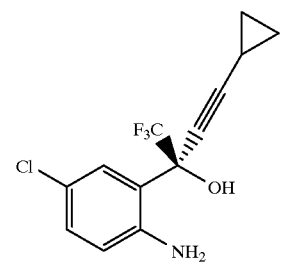

in an organic solvent with a base at a temperature of about 0° C. to about 25° C. under an inert atmosphere to produce a carbamate intermediate of formula

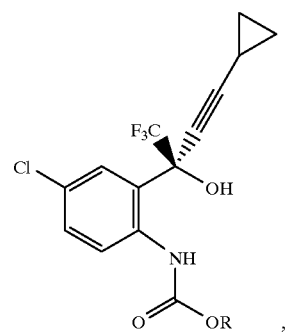

wherein R represents the aryl side chain of the chloroformate;

2) stirring the reaction mixture at about 20° C. to about 25° C. for about 1 to about 6 hours to complete the formation of the carbamate intermediate;

3) quenching the reaction with water or an aqueous base to produce a biphasic solution containing the 1,4-dihydro-2H-3,1-benzoxazin-2-one in the organic solvent phase;

4) stirring the biphasic mixture at about 20° C. to about 50° C. for about 1 to about 6 hours to complete the cyclization to the 1,4-dihydro-2H-3,1-benzoxazin-2-one; and 5) isolating the 1,4-dihydro-2H-3,1-benzoxazin-2-one from the organic phase.

2. The process for the preparation of a 1,4-dihydro-2H-3,1-benzoxazin-2-one as recited in claim 1, wherein the aryl group of the aryl chloroformate is defined as phenyl or naphthyl, which is optionally substituted with one, two or three substituents selected from the group consisting of: halo (F, Cl, Br, I), $CF_3$, $CO_2C_1$–$C_6$-alkyl, and $NO_2$.

3. The process for the preparation of a 1,4-dihydro-2H-3,1-benzoxazin-2-one as recited in claim 2, wherein the base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases.

4. The process for the preparation of a 1,4-dihydro-2H-3,1-benzoxazin-2-one as recited in claim 3, wherein the organic solvent is selected form the group consisting of: methyl t-butyl ether, toluene, tetrahydrofuran, acetonitrile, dimethylacetamide, N-methylpyrrolidinone, or a combination of said solvents.

5. The process for the preparation of a 1,4-dihydro-2H-3,1-benzoxazin-2-one as recited in claim 4, wherein the aryl group of the aryl chloroformate is defined as phenyl chloroformate, in which the phenyl is optionally substituted with one, two or three substituents selected from the group consisting of: halo (F, Cl, Br, I), CF₃, and NO₂.

6. The process for the preparation of a 1,4-dihydro-2H-3,1-benzoxazin-2-one as recited in claim 5, wherein the base is defined as a solid or solution of KOH, NaOH, K₂CO₃, Na₂CO₃, KHCO₃, NaHCO₃, or a combination of said bases.

7. The process for the preparation of a 1,4-dihydro-2H-3,1-benzoxazin-2-one as recited in claim 6, wherein the aryl group of the aryl chloroformate is defined as 4-nitrophenyl chloroformate.

8. A process for the preparation of a 1,4-dihydro-2H-3,1-benzoxazin-2-one of the formula

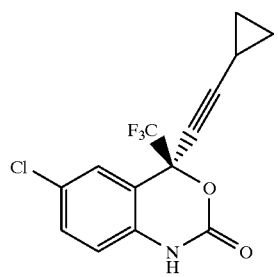

comprising the steps of:
  1) adding 4-nitrophenyl chloroformate in batches to a stirring mixture of an amino alcohol of formula

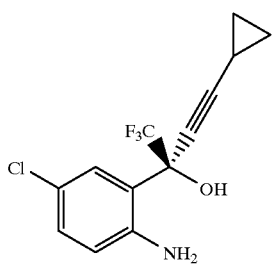

in methyl tert-butyl ether with an aqueous solution of KHCO₃ at a temperature of about 25° C. under a nitrogen atmosphere maintaining a pH of between about 8.5 and 4 to produce a carbamate intermediate of formula

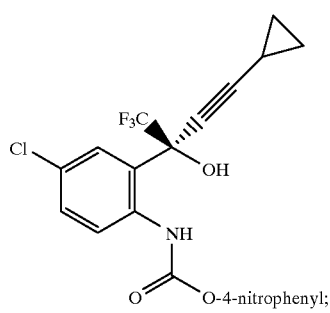

2) stirring the reaction mixture at about 20° C. to about 25° C. for about 2 hours to complete the formation of the carbamate intermediate;
  3) quenching the reaction with an aqueous KOH to a pH of about 11 and adding water to produce a biphasic mixture containing the 1,4-dihydro-2H-3,1-benzoxazin-2-one in the organic solvent phase;
  4) isolating the 1,4-dihydro-2H-3,1-benzoxazin-2-one from the organic phase.

9. A process for the preparation of a 1,4-dihydro-2H-3,1-benzoxazin-2-one of the formula

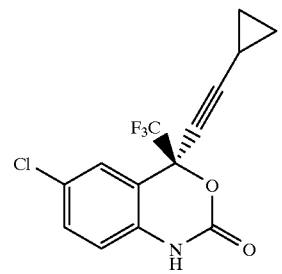

comprising the steps of:
  1) adding an aryl chloroformate to a stirring mixture of an amino alcohol of formula

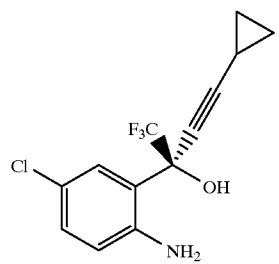

in an organic solvent at a temperature of about 0° C. to about 25° C. under an inert atmosphere to produce a carbamate intermediate of formula

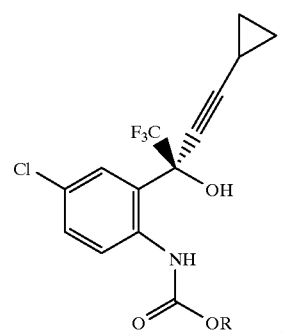

wherein R represents the aryl side chain of the chloroformate;
  2) stirring the reaction mixture at about 20° C. to about 25° C. for about 1 to about 6 hours to complete the formation of the carbamate intermediate;
  3) quenching the reaction with an aqueous base to produce a biphasic solution containing the 1,4-dihydro-2H-3,1-benzoxazin-2-one in the organic solvent phase;
  4) stirring the biphasic mixture at about 20° C. to about 50° C. for about 1 to about 6 hours to complete the cyclization to the 1,4-dihydro-2H-3,1-benzoxazin-2-one; and
  5) isolating the 1,4-dihydro-2H-3,1-benzoxazin-2-one from the organic phase.

10. The process for the preparation of a 1,4-dihydro-2H-3,1-benzoxazin-2-one as recited in claim 9, wherein the aryl group of the aryl chloroformate is defined as phenyl or naphthyl, which is optionally substituted with one, two or three substituents selected from the group consisting of: halo (F, Cl, Br, I), $CF_3$, $CO_2C_1$–$C_6$-alkyl, and $NO_2$.

11. The process for the preparation of a 1,4-dihydro-2H-3,1-benzoxazin-2-one as recited in claim 10, wherein the base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases.

12. The process for the preparation of a 1,4-dihydro-2H-3,1-benzoxazin-2-one as recited in claim 11, wherein the organic solvent is selected form the group consisting of: methyl t-butyl ether, toluene, or a combination of said solvents.

13. The process for the preparation of a 1,4-dihydro-2H-3,1-benzoxazin-2-one as recited in claim 12, wherein the aryl group of the aryl chloroformate is defined as phenyl chloroformate, in which the phenyl is optionally substituted with one, two or three substituents selected from the group consisting of: halo (F, Cl, Br, I), $CF_3$, and $NO_2$.

14. The process for the preparation of a 1,4-dihydro-2H-3,1-benzoxazin-2-one as recited in claim 5, wherein the base is defined as a solid or solution of KOH, NaOH, $K_2CO_3$, $Na_2CO_3$, $KHCO_3$, $NaHCO_3$, or a combination of said bases.

15. The process for the preparation of a 1,4-dihydro-2H-3,1-benzoxazin-2-one as recited in claim 14, wherein the aryl group of the aryl chloroformate is defined as 4-nitrophenyl chloroformate.

16. A process for the preparation of a 1,4-dihydro-2H-3,1-benzoxazin-2-one of the formula

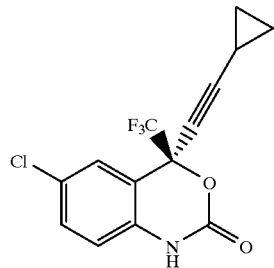

comprising the steps of:

1) adding an alkyl chloroformate to a stirring mixture of an amino alcohol of formula

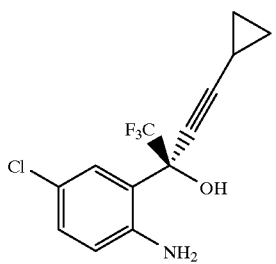

in a first organic solvent with a first base at a temperature of about 0° C. to about 25° C. under an inert atmosphere to produce a carbamate intermediate of formula

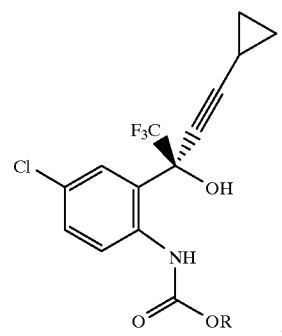

wherein R represents the alkyl side chain of the chloroformate;

2) stirring the reaction mixture at about 20° C. to about 25° C. for about 1 to about 30 hours to complete the formation of the carbamate intermediate;

3) isolating the organic phase containing the alkyl carbamate;

4) distilling about 90% to about 95% of the first organic solvent in vacuum and adding a counter solvent to isolate the solid alkyl carbamate;

5) adding a second organic solvent to the solid alkyl carbamate to form an alkyl carbamate solution;

6) reacting the alkyl carbamate solution with a second base at a temperature range of about 20° C. to about 25° C. for about 2 hours to about 30 hours to produce the 1,4-dihydro-2H-3,1-benzoxazin-2-one;

7) quenching the reaction mixture with an acid to produce a biphasic solution containing the 1,4-dihydro-2H-3,1-benzoxazin-2-one in the organic solvent phase;

8) isolating the 1,4-dihydro-2H-3,1-benzoxazin-2-one from the organic phase.

17. The process for the preparation of a 1,4-dihydro-2H-3,1-benzoxazin-2-one as recited in claim 16, wherein the alkyl group of the alkyl chloroformate is defined as $C_1$–$C_{10}$-alkyl, which is optionally substituted with one, two or three substituents selected from the group consisting of: halo (F, Cl, Br, I), $CF_3$, $C_3$–$C_7$-cycloalkyl, $CO_2C_1$–$C_6$-alkyl, and $NO_2$.

18. The process for the preparation of a 1,4-dihydro-2H-3,1-benzoxazin-2-one as recited in claim 17, wherein the first base is defined as a solid or solution of KOH, NaOH, LiOH, $K_2CO_3$, $Na_2CO_3$, $Li_2CO_3$, $KHCO_3$, $NaHCO_3$, $LiHCO_3$, or a combination of said bases.

19. The process for the preparation of a 1,4-dihydro-2H-3,1-benzoxazin-2-one as recited in claim 18, wherein the first organic solvent is selected form the group consisting of: methyl t-butyl ether, toluene, tetrahydrofuran, acetonitrile, or a combination of said solvents.

20. The process for the preparation of a 1,4-dihydro-2H-3,1-benzoxazin-2-one as recited in claim 9, wherein the counter solvent is heptane.

21. The process for the preparation of a 1,4-dihydro-2H-3,1-benzoxazin-2-one as recited in claim 20, wherein the second organic solvent is selected form the group consisting of: methyl t-butyl ether, toluene, tetrahydrofuran, $C_1$–$C_6$-alkanol, or a combination of said solvents.

22. The process for the preparation of a 1,4-dihydro-2H-3,1-benzoxazin-2-one as recited in claim 21, wherein the second base is defined as a solid or solution of $KOC_1$–$C_6$-alkyl, $NaOC_1$–$C_6$-alkyl, $LiOC_1$–$C_6$-alkyl, $KC_1$–$C_6$-alkyl, $NaC_1$–$C_6$-alkyl, $LiC_1$–$C_6$-alkyl, KHMDS, NaHMDS, LiHMDS, LDA or a combination of said bases.

23. The process for the preparation of a 1,4-dihydro-2H-3,1-benzoxazin-2-one as recited in claim 22, wherein the acid is selected form the group consisting of: HCl, $HNO_3$, $H_2SO_4$, and $CH_3CO_2H$.

24. The process for the preparation of 1,4-dihydro-2H-3,1-benzoxazin-2-one as recited in claim 23, comprising the additional step of: crystallizing the alkyl carbamate produced in step 4 from toluene-heptane or methyl t-butyl ether-heptane to produce the desired crystalline alkyl carbamate.

25. The process for the preparation of a 1,4-dihydro-2H-3,1-benzoxazin-2-one as recited in claim 24, wherein the alkyl chloroformate is defined as methyl or ethyl chloroformate.

26. The process for the preparation of a 1,4-dihydro-2H-3,1-benzoxazin-2-one as recited in claim 25, wherein the organic solvent (or solvent mixture) is selected form the group consisting of: methyl t-butyl ether; methyl t-butyl ether and tetrahydrofuran; and methyl t-butyl ether and ethanol.

27. The process for the preparation of a 1,4-dihydro-2H-3,1-benzoxazin-2-one as recited in claim 26, wherein the base is defined as a solid or solution of $KHCO_3$ and KOH, $KHCO_3$ and $K_2CO_3$, or $KHCO_3$, and $LiO^tBu$.

* * * * *